United States Patent [19]

Young et al.

[11] Patent Number: 5,558,984
[45] Date of Patent: Sep. 24, 1996

[54] AUTOMATED SYSTEM AND PROCESS FOR HETEROTROPHIC GROWTH OF PLANT TISSUE

[75] Inventors: Roy E. Young, Six Mile, S.C.; S. Andrew Hale, Garner, N.C.

[73] Assignee: Clemson University, Clemson, S.C.

[21] Appl. No.: 253,734

[22] Filed: Jun. 3, 1994

[51] Int. Cl.⁶ .............................. C12Q 3/00; A01G 31/00
[52] U.S. Cl. .................. 435/3; 435/240.1; 435/240.241; 435/240.45; 435/287.1; 435/286.5; 435/292.1; 47/60; 47/62; 47/48.5; 47/DIG. 9
[58] Field of Search ................................ 435/29, 34, 39, 435/284, 289, 291, 3, 286.5, 287.1, 292.1, 297.5, 240.2, 240.241, 240.4, 240.45, 240.1; 422/62, 81, 108, 110, 116, 119; 436/50, 55; 47/60, 62, 1.4, 48.5, DIG. 9, 10

[56] References Cited

U.S. PATENT DOCUMENTS

| | | |
|---|---|---|
| 3,578,431 | 5/1971 | Ingestad et al. . |
| 4,043,903 | 8/1977 | Dor . |
| 4,320,594 | 3/1982 | Raymond .................................. 47/1.4 |
| 4,382,348 | 5/1983 | Kitsu et al. . |
| 4,531,324 | 7/1985 | Yang . |
| 4,669,217 | 6/1987 | Fraze ........................................... 47/64 |
| 4,754,877 | 7/1988 | Johnansson, et al. . |
| 4,908,315 | 3/1990 | Kertz . |
| 4,934,096 | 6/1990 | Bentvelsen . |
| 4,975,377 | 12/1990 | Key . |
| 5,001,859 | 3/1991 | Sprung . |
| 5,049,505 | 9/1991 | Sei ......................................... 435/311 |
| 5,054,234 | 10/1991 | Cassells . |
| 5,088,231 | 2/1992 | Kertz . |
| 5,104,527 | 4/1992 | Clinkenbeard . |
| 5,119,588 | 6/1992 | Timmis . |
| 5,139,956 | 8/1992 | Schick et al. . |
| 5,171,683 | 12/1992 | Kertz . |
| 5,184,420 | 2/1993 | Papadopoulos et al. .................. 47/62 |
| 5,186,895 | 2/1993 | Onofusa et al. . |
| 5,212,906 | 5/1993 | Okuno, et al. . |
| 5,225,342 | 7/1993 | Farrell . |

OTHER PUBLICATIONS

Plastic Films As Plant Tissue Culture Vessels (ASAE meeting presentation booklet, Dec. 1990 International Winter Meeting, Chicago, Illinois).

Plant Micropropatation Bioreactor Development (ASAE meeting presentation Dec. 17–20, 1991 Chicago, Illinois.

Bioreactor Development For Continual–Flow, Liquid Plant Tissue Culture Acta Horticulturae 319, 1992 Transplant Production Systems (pp. 107–112).

Phytasource Membrane Rafts, Sigma Chemical Company, vol. 1, No. 1 pp. 1–8, Spring 1990.

*Primary Examiner*—David A. Redding
*Attorney, Agent, or Firm*—Dority & Manning, P.A.

[57] ABSTRACT

A micropropagation system and process for promoting the growth of plant tissue in a sterile environment is provided. The system includes a bioreactor in which the explant tissue is contained and grown. A plurality of fluid reservoirs are connected to the bioreactor for supplying sugar, nutrients, hormones, and water to the plant material. A controller and an analyzer are also included for automating the system by controlling flow rates and by monitoring media concentrations and levels within the bioreactor. Specifically, the controller is capable of monitoring system conditions and making the desired corrections by receiving data from the chemical analyzer. In particular, the controller is capable of calculating and maintaining volume levels of liquid growth media within the bioreactor chamber and maintaining the proper concentrations and proportions of components in the growth media.

21 Claims, 5 Drawing Sheets

AUTOMATED SYSTEM AND PROCESS FOR HETEROTROPHIC GROWTH OF PLANT TISSUE

BACKGROUND OF THE INVENTION

The present invention relates generally to a plant propagation system, and more particularly to an automated system and process for promoting heterotrophic growth of plant tissue.

Micropropagation, sometimes referred to as tissue culture propagation, is the process of growing new plants from a piece of plant tissue that has been extracted from a parent plant with desired characteristics. Micropropagation has recently grown in popularity as a preferred plant propagation technique for a wide range of horticultural crops because of high production efficiency and greater uniformity of the resulting plants. The process results in the mass reproduction of plants having certain desirable characteristics since substantially all of the plants produced are genetically identical to and have all of the desirable traits of the parent. Micropropagation is an especially useful process for genetically engineered plants, high-value transplants, seedless fruits and vegetables, certified disease free plant material and all other plants that cannot be produced from seed economically or uniformly.

In general terms, micropropagation typically includes first selecting a parent plant. The parent plant should be healthy and should have the desired traits that are needed in the next generation plants. A tissue sample is then extracted from the parent. The sample is typically meristematic tissue which is undifferentiated tissue capable of dividing and giving rise to other meristemic tissue as well as specialized tissue types. Meristematic tissue is found in growth areas such as at the tips of stems or at lateral buds. The tissue sample (explant) is disinfected and then placed in a controlled environment and supplied essential nutrients for promoting growth.

Growth of the plant tissue sample into a small plant occurs in four commonly referred to stages. First, growth of the explant is established in a sterile environment. Second, high proliferation of explant is promoted by repeated selection of small pieces of tissue containing vegetative buds, or other specialized propagative structures (e.g., bulbets, protocorm-like bodies (PLB), microtubers, somatic embryos). The third stage involves forming a shoot from the vegetative bud. The fourth stage involves forming a root on the shoot, thereby completing the development of a whole plant from the plant tissue.

During the first and second stages of growth, the plant tissue is made up of small rapidly dividing cells with high metabolic requirements for energy. The tissue is incapable of carrying out adequate photosynthesis to meet this high demand.

Consequently, initial growth of the tissue is done heterotrophically. Heterotrophic growth is where the organism obtains nourishment and energy from the ingestion and breakdown of organic matter. During this phase, the plant tissue is typically not exposed to light and is fed a growth medium containing organic carbon. The organic carbon is usually obtained from sugars such as sucrose.

In the third stage of growth, leaves and shoots expand and the plant tissue becomes more capable of photosynthesizing. The plant tissue, when exposed to light, gases, water and essential nutrients, derives energy photoautotrophically through the process of photosynthesis. Photoautotrophic growth is where an organism synthesizes organic nutrients by deriving energy from light. In other words, during autotrophic growth, the plant tissue is capable of making its own food which it cannot do adequately during the other stages.

The focus of the process and system of the present invention is the initial heterotrophic growth of plant tissue. Generally, this stage of growth involves placing explant tissue in contact with a nutrient medium formulated to provide everything to which the tissue would have access if it were part of a complete plant. Hormones can also be added to the nutrient growth media in order to stimulate desired growth responses.

Traditionally, the heterotrophic growth of plant tissue has been done in a batch type arrangement. Specifically, tissue samples have been placed on agar or semisolid mediums for providing nutrients and organic carbon to the plant material. Once the nutrient medium is spent, the plant tissue is manually transplanted to new media for continued growth. However, this process is not only expensive and time consuming but can lead to contamination of the plant material since aseptic conditions are almost impossible to maintain.

Recently, attempts have been made to develop a plant micropropagation system that does not rely on semisolid mediums, using instead a liquid nutrient solution. Examples of plant growth systems are illustrated in U.S. Pat. No. 3,578,431 to Ingestad, et al., U.S. Pat. No. 4,320,594 to Raymond, U.S. Pat. No. 4,669,217 to Frase, U.S. Pat. No. 4,934,096 to Bentvelsen, U.S. Pat. No. 5,049,505 to Sei, U.S. Pat. No. 5,184,420 to Papadopoulos, et al., U.S. Pat. No. 5,104,527 to Clinkenbeard, U.S. Pat. No. 5,139,956 to Schick, et al., and U.S. Pat. No. 5,186,895 to Onofusa, et al. However, as will be apparent to one skilled in the art the particular features and aspects of the present invention remain absent from the prior art.

SUMMARY OF THE INVENTION

The present invention recognizes and addresses various disadvantages and drawbacks of prior art constructions and methods.

Accordingly, it is an object of the present invention to provide a plant micropropagation system.

It is another object of the present invention to provide a new method for propagating plant tissue.

It is a further object of the present invention to provide a plant tissue system for promoting heterotrophic growth of the plant material.

It is another object of the present invention to provide a micropropagation system for automatically growing plant tissue.

It is still another object of the present invention to provide a plant micropropagation system for promoting the growth of plant tissue using a liquid nutrient solution.

It is another object of the present invention to provide a plant micropropagation system that can automatically monitor and change the nutrient and sugar concentrations of a liquid nutrient solution fed to the plant tissue.

It is another object of the present invention to provide an automated system and process for promoting the heterotrophic growth of plant tissue in an aseptic environment.

These and other objects are achieved by providing an automated micropropagation system and process for promoting the heterotrophic growth of plant tissue. The plant micropropagation system of the present invention automatically monitors and controls the concentration of selected components in a liquid nutrient solution without disturbing the growing explant tissue. Further, the micropropagation system provides an aseptic environment for the growing plant tissue, preventing contamination by microorganisms.

The micropropagation system of the present invention includes a bioreactor for holding growing plant tissue therein. The bioreactor allows gas exchange without permitting the influx of biological contaminants. The bioreactor is designed to hold a predetermined volume of a liquid growth solution fed to the plant material. A plurality of containers are connected to the bioreactor for feeding various solutions to the plant. For instance, the system can include a container for holding a sucrose solution, a container for holding a liquid nutrient and hormone solution, and a container for holding water. The containers are connected to a valve arrangement which is in turn connected to a supply control pump for pumping various amounts of each solution to the bioreactor.

A waste control pump is also connected to the bioreactor for pumping spent growth solution from the reactor to a waste container. By controlling the flow rates of the supply control pump in conjunction with the flow rate of the waste control pump, the volume of liquid growth solution contained within the bioreactor can be determined and maintained.

The micropropagation system also includes a media circulation pump which circulates fluid within the bioreactor for mixing the various components of the liquid growth solution and for preventing any settling of the various components. A chemical analyzer periodically obtains a sample from the liquid growth solution circulated from the bioreactor. The analyzer then automatically analyzes the sample for determining the concentration of a particular component. For instance, the analyzer may be selected for monitoring sucrose concentration within the growth solution.

The analytical results obtained by the chemical analyzer are then electronically fed to a microprocessor such as a control computer which accepts and stores the data. The data is then fed into a computer program for monitoring the concentration of the component tested for. The control computer automatically controls the valves, the supply control pump, and the waste control pump for feeding the individual solutions to the bioreactor. As such, the control computer automatically controls the volume and nutrient composition of the liquid growth solution fed to the bioreactor.

Using the system and process of the present invention, the heterotrophic growth of explant tissue is completely automated. The tissue is grown in an aseptic environment without having to be transplanted or disturbed. Once the tissue has developed sufficiently or has developed the capability to rely solely on autotrophic growth, the tissue can be moved or transplanted to a greenhouse environment for further growth as desired.

Other objects, features and aspects of the present invention are discussed in greater detail below.

BRIEF DESCRIPTION OF THE DRAWINGS

A full and enabling disclosure of the present invention, including the best mode thereof, to one skilled in the art is set forth more particularly in the remainder of the specification, including reference to the accompanying figures in which.

Figure 1:
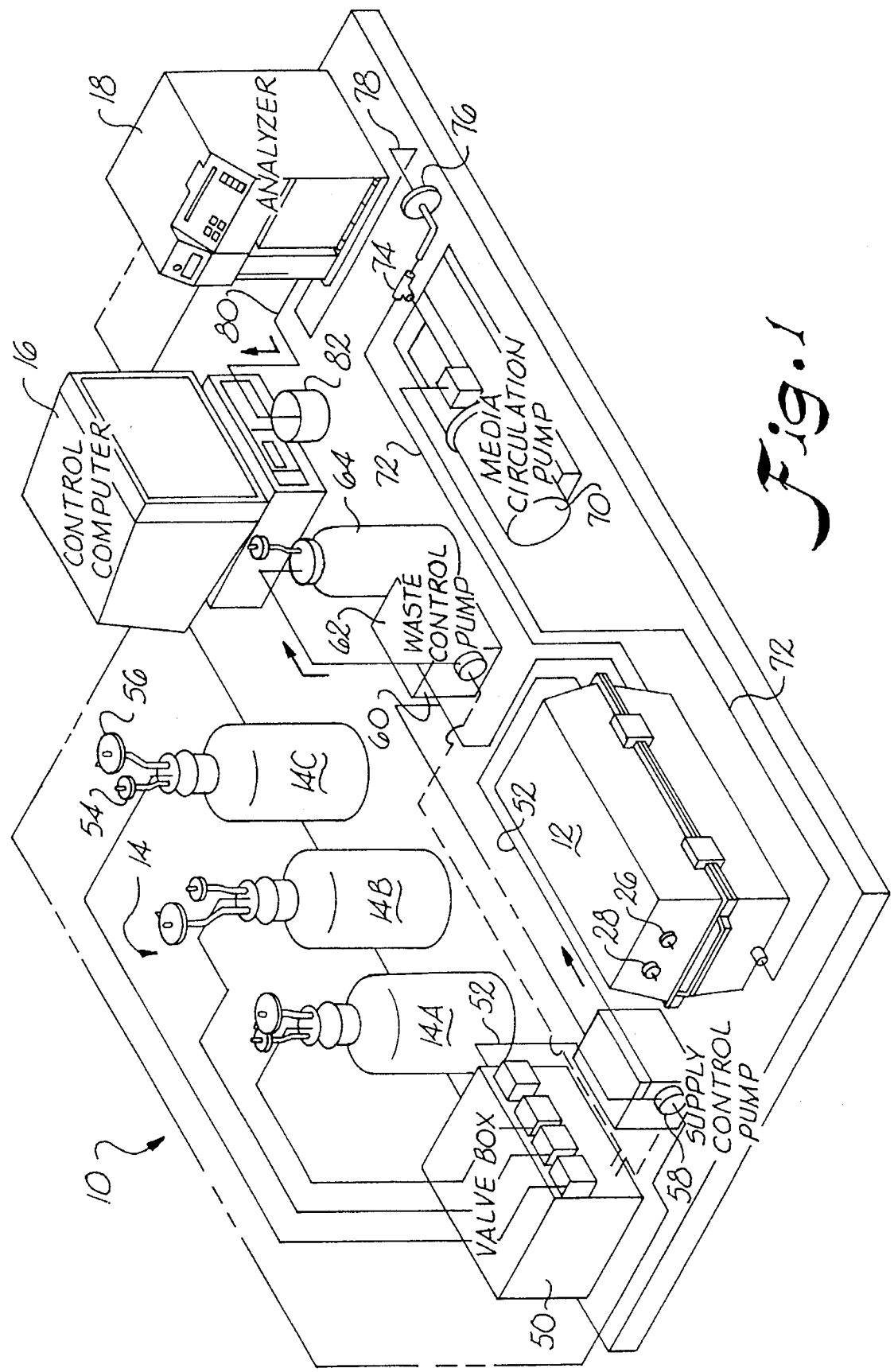
FIG. 1 is a perspective view of one embodiment of a plant micropropagation system in accordance with the present invention.

Repeat use of reference characters in the present specification and drawings is intended to represent same or analogous features or elements of the invention.

DETAILED DESCRIPTION OF PREFERRED EMBODIMENTS

It is to be understood by those of ordinary skill in the art that the present discussion is a description of exemplary embodiments only, and is not intended as limiting the broader aspects of the present invention, which broader aspects are embodied in the exemplary constructions.

Referring to FIG. 1, one embodiment of an automated micropropagation system in accordance with the present invention is illustrated. Generally, micropropagation system 10 includes a bioreactor 12 where viable plant tissue is kept. A plurality of reservoirs generally 14 are connected to the bioreactor for supplying various solutions or subcomponents to the growing plant tissue. In a preferred embodiment, three reservoirs are provided for containing and supplying a sucrose solution, a mineral salt and hormone solution, and distilled water. A controller 16, such as a microprocessor or computer, and a chemical analyzer 18 are also included for automating the system by controlling flow rates and by monitoring media concentrations and levels within bioreactor 12. Specifically, small aliquots of bioreactor media are withdrawn from bioreactor 12 at periodic intervals. Analyzer 18 then determines the concentration of a particular component such as sucrose. This analysis is then sent to controller 16 and entered into a program.

Controller 16 is capable of monitoring system conditions and making the desired corrections. For instance, controller 16 is capable of calculating and maintaining correct volume levels of growth media within the bioreactor chamber and maintaining the proper concentrations and proportions of components in the media as will be described in more detail hereinafter.

Before describing the operation of micropropagation system 10 in detail, each component of the system will be discussed individually. Referring to FIG. 1 and more particularly to FIG. 2 a suitable bioreactor for use in the present invention is illustrated. Bioreactor 12 is for holding a plurality of explant tissues for heterotrophic growth. Any suitable container that is capable of receiving and circulating a liquid growth medium without allowing the infestation of microorganisms can be used in the process of the present invention. One preferred embodiment of a bioreactor 12 is illustrated in the figures.

Figure 2:
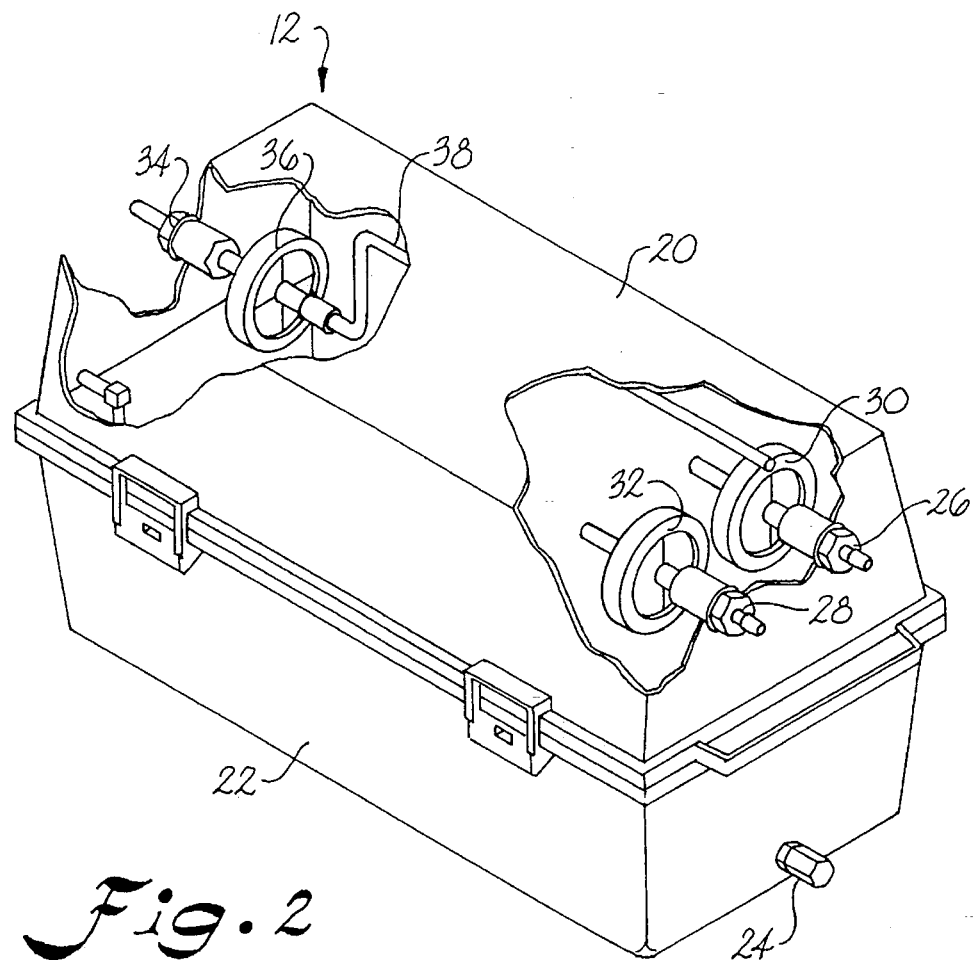
FIG. 2 is a perspective view with cutaway portions of a bioreactor that may be used in the process of the present invention.

As shown in FIG. 2, the bioreactor 12 includes a top portion 20 sealed to a bottom portion 22. Preferably bioreactor 12 is made from a transparent material to allow sufficient light transmission as well as to allow visual observation of the plant tissue during growth. A similar container as shown in FIG. 2 is marketed under the name BIO-SAFE CARRIER by Nalgene, Inc. The BIO-SAFE CARRIER is made from a polycarbonate material and can be modified for use in the process of the present invention.

Bioreactor 12 as shown includes separate media inlet and outlet ports, and a sterile gas exchange system. An inlet or outlet port 24 as desired is shown in FIG. 2 located on bottom portion 22 of bioreactor 12. The embodiment illustrated includes two gas outlets 26 and 28 located on top portion 20. Gas outlets 26 and 28 are in communication with respective gas outlet filters 30 and 32. Gas outlet filters 30 and 32 allow gases given off by the plant tissue to be released from bioreactor 12 without allowing contaminants such as microorganisms to diffuse therein. Gas outlet filters 30 and 32 each contain a hydrophobic filter element to prevent the loss of moisture from the bioreactor chamber. Such filters are sold by Gelman Sciences.

Also included in bioreactor 12 is a gas inlet 34 and a corresponding gas inlet filter 36. Further included is a gas distribution manifold 38. Manifold 38 can be made from a polypropylene tubing with holes drilled along its length for distributing incoming gas. Gas inlet 34 can be connected to a type of gas reservoir such as a carbon dioxide tank if desired. Carbon dioxide is necessary for plant processes and can be supplemented if needed. Of course, any gas can be fed to bioreactor 12 depending upon the particular conditions. Further, more or less gas inlets or gas outlets can be placed upon the bioreactor. In another embodiment, a gas permeable film can be used to form a section of the bioreactor.

Figure 3:
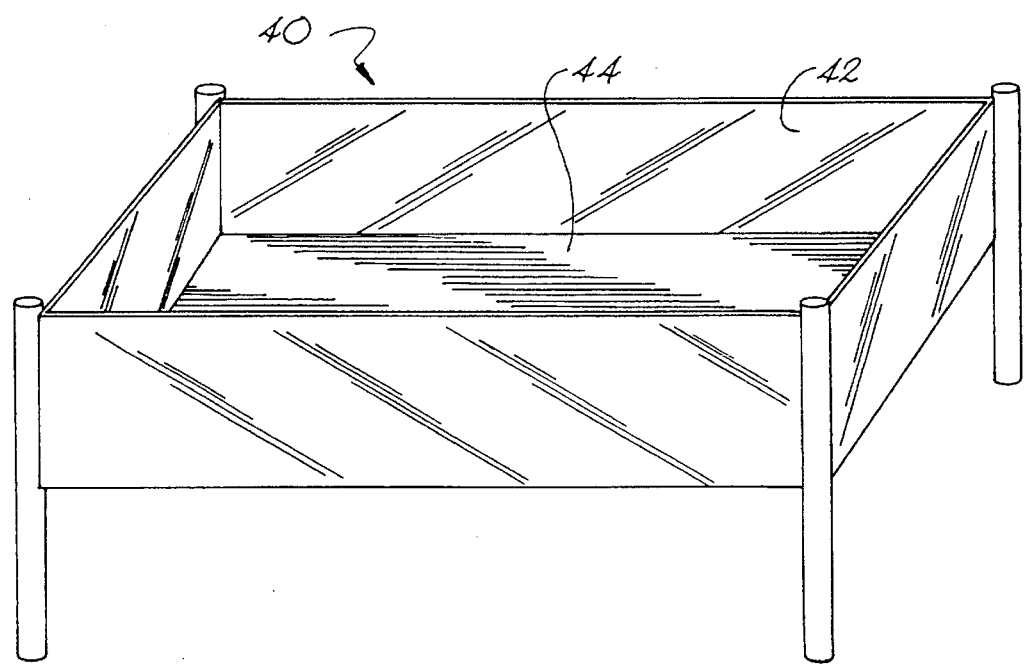
FIG. 3 is a perspective view of a membrane raft that may be used in the process of the present invention.

Bioreactor 12 is designed to contain explant tissue. Also, various ports are provided for allowing a liquid growth media to circulate and for allowing needed gas exchange without allowing the influx of contaminants. Preferably, the plant tissue is grown on membrane rafts as illustrated in FIG. 3. A membrane raft generally 40 includes a support structure 42 having a membrane 44 for supporting the plant tissue. Membrane 44 can be made from a microporous material capable of allowing controlled liquid diffusion therethrough. In one example, membrane 44 can be made from a stretched polypropylene such as CELGUARD film. Similar membrane rafts are available through Sigma Chemical Company from St. Louis, Mo.

Membrane raft 40 can support explant tissue therein and can be placed within bioreactor 12. Membrane raft 40 is buoyant. As such, raft 40 floats on top of the growth media that is circulated within bioreactor 12. The plant tissue is capable of absorbing the growth media through membrane 44 for promoting optimum growth. Since the plant tissue is not submerged, the tissue is capable of also absorbing optimum amounts of gases. Bioreactor 12 can be designed to hold multiple rafts as desired.

Referring to FIG. 1, a plurality of reservoirs 14 are each connected to a valve box 50 feeding into a single bioreactor inlet 52. Various amounts of reservoirs and solutions can be connected to micropropagation system 10 as desired. The number and concentration of the solutions chosen will depend on various factors including system parameters and the particular type of plants being grown. The embodiments illustrated in FIG. 1 showing three reservoirs 14A, 14B, and 14C will accommodate most micropropagation systems. Specifically, reservoir 14A is for containing a sucrose solution, reservoir 14B is for containing a nutrient salt and hormone solution, and reservoir 14C is for containing distilled and deionized water. If needed, reservoir tanks 14 can include magnetic stir plates or similar devices for keeping the solutions mixed properly.

As shown, each reservoir tank 14 includes a gas vent 54 and a media sterilization filter 56. Similar to the gas exchange vents on bioreactor 12, gas vent 54 can be designed to allowed gases to enter or exit reservoir 14 without allowing contaminants therein.

Media sterilization filter 56 is for replenishing the solution supply contained within the reservoirs. In particular, filter 56 allows liquids to pass therethrough without permitting the passage of microorganisms and other contaminants. As such, solution reservoirs 14 can be resupplied with solution without the threat of microbial infestation.

In supplying the various solutions to bioreactor 12, reservoirs 14 first supply the respective solutions to valve box 50. Valve box 50 is preferably comprised of a solenoid valve system capable of being controlled electronically. The valve system includes a valve corresponding to each solution. A supply control pump 58 pumps one solution at a time to bioreactor 12 via bioreactor inlet tube 52. By only pumping one media component at a time, various formulation changes can be made. In particular, supply control pump 58 is calibrated to pump at a particular flow rate for determining the amount of each component as it is fed to bioreactor 12.

Micropropagation system 10 also includes a bioreactor outlet 60, a waste control pump 62 and a waste container 64. Waste control pump 62 is for pumping spent growth media from bioreactor 12 to waste container 64 for proper disposal. Preferably, supply control pump 58 and waste control pump 62 are peristaltic pumps which are pumps in which fluid is forced along by waves of contractions produced mechanically on flexible tubing. In this arrangement the threat of contamination through the pumps is minimized. Pumps 58 and 62 can have variable flow rates that are capable of being controlled electronically. By assuming that the explant tissue within bioreactor 12 will not absorb significant amounts of growth media, the two pumps working in conjunction can maintain a constant fluid level within bioreactor 12. Of course, volume sensors could also be placed within bioreactor 12 for more precisely monitoring and controlling fluid levels.

Also included within micropropagation system 10 is a media circulation pump 70 connected to a circulation loop 72 which enters and exits bioreactor 12. Circulation loop 72 and circulation pump 70 are designed to continuously circulate the liquid growth media within bioreactor 12. As described above, each solution contained within reservoir tanks 14 is fed to bioreactor 12 one at a time. Circulation loop 72 continuously mixes the components of the liquid growth media and prevents any settling of the components.

Connected to circulation loop 72 is a T-connector 74 leading to analyzer 18 via a sample tube 78. Between T-connector 74 and analyzer 18 there is also a sample filter 76 which permits fluid to flow into sample tube 78 without allowing microorganisms or other contaminants to enter circulation loop 72.

During operation, at predetermined intervals, a sample of bioreactor growth media is fed to chemical analyzer 18. Analyzer 18 can analyze the sample and determine the concentration of a particular component. For instance in most micropropagation systems, it is important to maintain the sugar or sucrose concentration in the growth media within preset limits. A suitable analyzer capable of determining sugar concentrations within a liquid media is the Model 2700 Biochemical Analyzer marketed by Yellow Springs Instruments, Inc. from Yellow Springs, Ohio. Of course, other types of analyzers could be used within the process of the present invention to monitor for other components if necessary. Also, more than one analyzer could also be included within the system to monitor more than one component.

After a sample of the growth media is analyzed, the sample leaves analyzer 18 out a sample waste tube 80 and into a sample waste 82 for proper disposal.

In order to ensure that accurate data is obtained from chemical analyzer 18, sample tube 78 can be disinfected at routine intervals. In particular, sample tube 78 from sampling filter 76 to analyzer 18 is vulnerable to contamination. To disinfect sample tube 78 a dilute bleach solution can be rinsed therethrough. Also, analyzer 18 should be calibrated on a regular basis.

Chemical analysis performed by analyzer 18 can be electronically transmitted to controller 16 which can receive, store and process the data using specially developed software. From the results obtained from analyzer 18, controller 16 can control the amount of various solutions contained within reservoirs 14 sent to bioreactor 12 and can control the amount of growth media withdrawn from the bioreactor and disposed. By controlling the valves and the pumps within the system, controller 16 can maintain optimum concentrations and levels of the growth media within the bioreactor for promoting the growth of the explant tissue.

In order to describe and properly understand the computer software developed for controller 16 for controlling micropropagation system 10, the following description is included. Specifically, the following detailed description relates to micropropagation system 10 containing three reservoir tanks 14A, 14B, and 14C as shown. Tank 14A contains a sucrose solution, tank 14B contains a Murashige and Skoog tissue culture media formulation containing liquid nutrients and various plant hormones while reservoir tank 14C contains distilled deionized water. The following control parameters programed into the software are merely exemplary but are believed to provide optimal conditions for many plant micropropagation systems.

Figure 4:
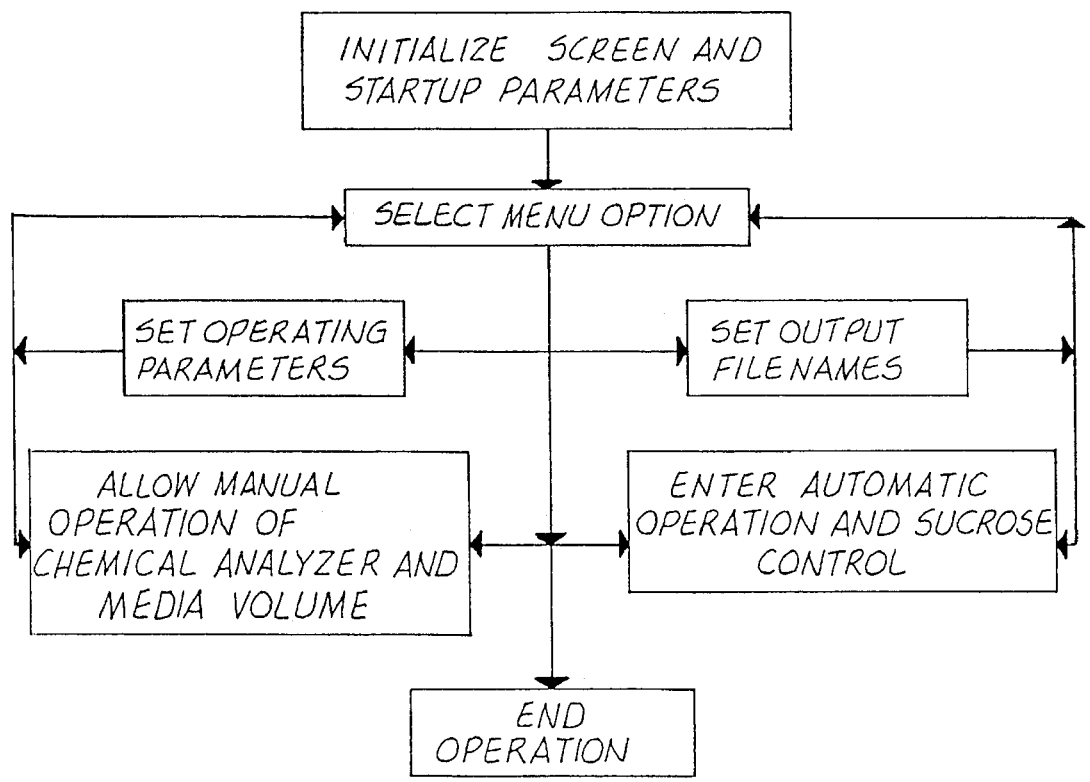
FIG. 4 is a flow chart pertaining to the computer software developed for the process of the present invention.

The software loaded into controller 16 includes an algorithm for automatic control of bioreactor sucrose level and replenishment of sampled media volumes. The computer program, which is included herewith as Attachment A written in source code, includes four separate modules operated through a menu driven user interface as shown in FIG. 4. Upon start up, the computer screen is first initialized to display the system operating parameters, the incoming data from chemical analyzer 18, any operating problems detected, and a user menu. From the menu, an operator can modify the control and operational parameters, can change the names of the output data and calibration information files, can switch to manual control of bioreactor media volume and chemical analyzer operation, and can enter automatic system operation or can exit the software completely.

Figure 5:
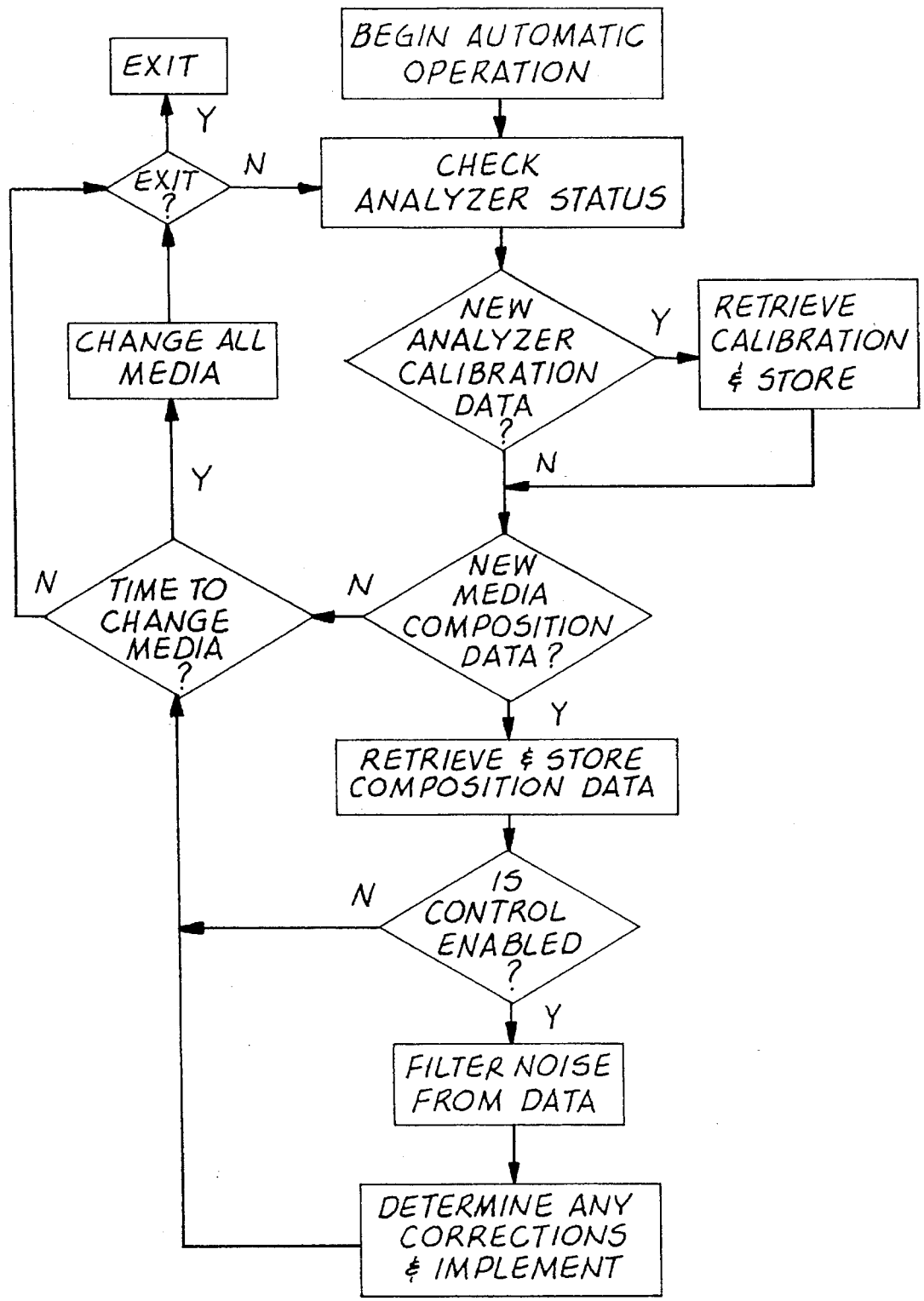
FIG. 5 is another flow chart outlining the automatic control operation of computer software developed for the present invention.

Upon entering an automatic operation of micropropagation system 10 the developed software functions as outlined in FIG. 5. Once automatic operation has been selected, the control computer enters a data acquisition and control loop in which it checks the status of the chemical analyzer to determine if new calibration or media composition data has been obtained. Basically, this new data is generated by the chemical analyzer while the computer is awaiting the next data point. The detection of new data results in its transmission to the control computer and permanent storage on disk.

Acquisition of a new sucrose composition measurement triggers execution of the control functions. The system first checks to see if automatic control has been disabled by an operator. This option is available for allowing periodic maintenance of the chemical analyzer without effecting the operation of the micropropagation system. If this is found not to be the case, incoming data is compared with prior readings in order to filter "noise" from the data stream. Noise data refers to data that is not consistent with previous measurements.

The built in filter consists of the calculation of a moving average for data collected over a particular period of time. In one embodiment, micropropagation system 10 was programmed so that chemical analyzer 18 receives and analyzes a sample every 3 hours. The moving average, as just described, can then be set for data collected over a 12 hour period. Outlier data, defined as that with a 10 percent or greater variation from the prior reading, is removed from the data stream prior to average computation. If subsequent data points show a previously detected outlier to be the start of a step change in media sucrose concentration, the reading is placed back in the average data stream at the point where it was removed. In the event of outlier detection, sucrose control is temporarily disabled by input to the control algorithm of a bioreactor media sucrose level equal to the desired setpoint, minimizing sucrose correction errors. The sucrose concentration moving average is otherwise used.

Following filter screening of any sucrose concentration data, another control algorithm is executed to determine if corrections to either the bioreactor media sucrose level or the media volume are needed. The multi-input/multi-output system operates with two reference set points for media sucrose concentration and volume. Set point threshold levels of plus or minus 5 percent for sucrose and plus or minus 2.5 percent for volume are used to determine if corrections are necessary. Of course, the threshold level setpoints can be set to any desired range. If any of the four threshold values for sucrose concentration or volume are violated, an air flag is generated calling for a system correction in which both sucrose and volume levels are adjusted to their desired set points.

Three governing equations describe the sucrose concentration and bioreactor media volume, (two describing the concentration of media components and one characterizing bioreactor volume). The equations are as follows:

$$TVOL = CVOL + SAVOL + MSAVOL + WAVOL - OVOL$$

where
TVOL=target media volume setpoint (ml),
CVOL=current bioreactor chamber media volume (ml),
SAVOL=volume of supply sucrose to be added to bioreactor chamber (ml),
MSAVOL=volume of supply Murashige and Skoog salts and hormones to be added to the bioreactor chamber (ml),
WAVOL=volume of distilled, deionized water to be added to the bioreactor chamber (ml),
OVOL=volume of media to remove from the bioreactor chamber (ml), $$TSCONC = \frac{CSCONC*CVOL + SSCONC*SAVOL}{CVOL + SAVOL + MSAVOL + WAVOL}$$

where
TSCONC=target media sucrose concentration (g/l),

CSCONC=current concentration of sucrose in the bioreactor media (g/l),

SSCONC=concentration of supply sucrose solution (g/l);

$$TMSCONC = \frac{CMSCONC*CVOL + SMSCONC*MSAVOL}{CVOL + SAVOL + MSAVOL + WAVOL}$$

where

TMSCONC=target concentration setpoint of Murashige and Skoog salts and hormones (percent full strength formulation), CMSCONC=current concentration of Murashige and Skoog salts and hormones (percent full strength formulation), SMSCONC=concentration of supply Murashige and Skoog salts and hormones (percent full strength formulation)

Upon detection of a threshold violation, the above equations are solved to determine the quantities of sucrose, water, and Murashige and Skoog salts and hormones to be added to the bioreactor as well as the volume of any excess, or overflow media to be removed. In this embodiment, because the current concentrations of Murashige and Skoog salts and hormones are not monitored, they are assumed to remain at 100 percent at all times. The presence of four unknown values and only three equations necessitates that a variable's value be assumed before a solution can be computed. The following shows the presumptions made for all various controlled scenarios.

| Threshold Violation | Low Sucrose | High Sucrose |
|---|---|---|
| Low Volume | OVOL or WAVOL = 0 | SAVOL or OVOL = 0 |
| High Volume | WAVOL = 0 | SAVOL = 0 |

In each case, one control variable can be safely assumed to be zero due to the circumstances present. For example, if sucrose concentration and media volume both are above their set points, no sucrose needs to be added to the bioreactor. In instances when two variables might be able to be assumed to be zero, the parameter first listed above is initially set to zero. If the assumption is in error, the second variable is found to be negative. The assumption is then changed and the equation once again solved.

Following the determination of an acceptable control solution, the computer signals the media supply valves at the valve box 50 and actuates supply control pump 58 so that desired volumes of sucrose, Murashige and Skoog salts and hormones, and water can be dispensed in the bioreactor chamber. Simultaneously, waste control pump 62 can be controlled to remove any excess media. To prevent composition corrections from temporarily filling bioreactor chamber with a media volume above the high volume threshold which might possibly harm the explant tissue, the corrections are first implemented with excess media volume first being removed followed by a recalculation of the control solution. When system corrections are made, all prior sucrose concentration data used for filtering are discarded to avoid including incorrect readings in the moving average.

Further, the automatic operation mode also includes a desired time period for complete media replenishment. The software monitors the time period between replenishment cycles. When it is determined that complete media replenishment is necessary, all spent media is pumped out of the bioreactor chamber and fresh media is dispensed through computer controlled mixing of the three stock solutions.

Many variations can be included within micropropagation system 10 in addition to the above described process. For instance, other control devices may be placed within the system for monitoring system conditions. Such instruments may include a pH meter, an oxygen or carbon dioxide analyzer, or flow meters which are capable of sending electronic signals to controller 16 which can then be used to make corrections within the system. Also, other similar analyzers can be included within the system for monitoring nutrient concentration, potassium concentration, phosphate concentration, or the like. Although not necessary, these additional features can be added depending upon the particular type of plant being grown and the growth conditions.

The present invention may be better understood by reference to the following examples.

EXAMPLES

Testing of the micropropagation system of the present invention was conducted through two separate experiments. The first was designed to demonstrate the controller's ability to respond to setpoint changes and detected errors in media volume and sucrose levels. In the second experiment, system performance during culture conditions was examined by placing Stage 1, *Nicotiana tabacum L. cv. Burley* 21 (tobacco) tissue in the bioreactor and controlling sucrose concentration throughout a 28-day culture cycle.

EXAMPLE I

In this experiment, a series of setpoint changes and disturbances were imposed on the control system while monitoring controller performance over time. The micropropagation system was operated without explant tissue. Following setup, the system was placed under automatic control with a sucrose concentration setpoint of 30 g/l and a media volume setpoint of 385 ml. The following step changes in the sucrose concentration setpoint were made over time: 35, 30, 27 and 34 g/l. Two disturbances were also introduced into the system, one of which coincided with a setpoint change, by pumping extra stock sucrose solution into the bioreactor chamber.

Prior to setup, all components of the liquid/membrane bioreactor, except media stock solutions and sampling filters, were assembled and autoclave sterilized at 121 degrees C. and 124 kPa pressure for 15 minutes. Stock solutions of 200 g/l sucrose, 300 percent (12.99 g/l) Murashige and Skoog salts and distilled, deionized water were subsequently introduced into the supply reservoirs using a manufacturer-presterilized media filter connected to the system under a laminar flow hood. Sampled media sucrose concentrations, calculated bioreactor media volumes (CVOL), and all control actions were recorded.

Figure 6:
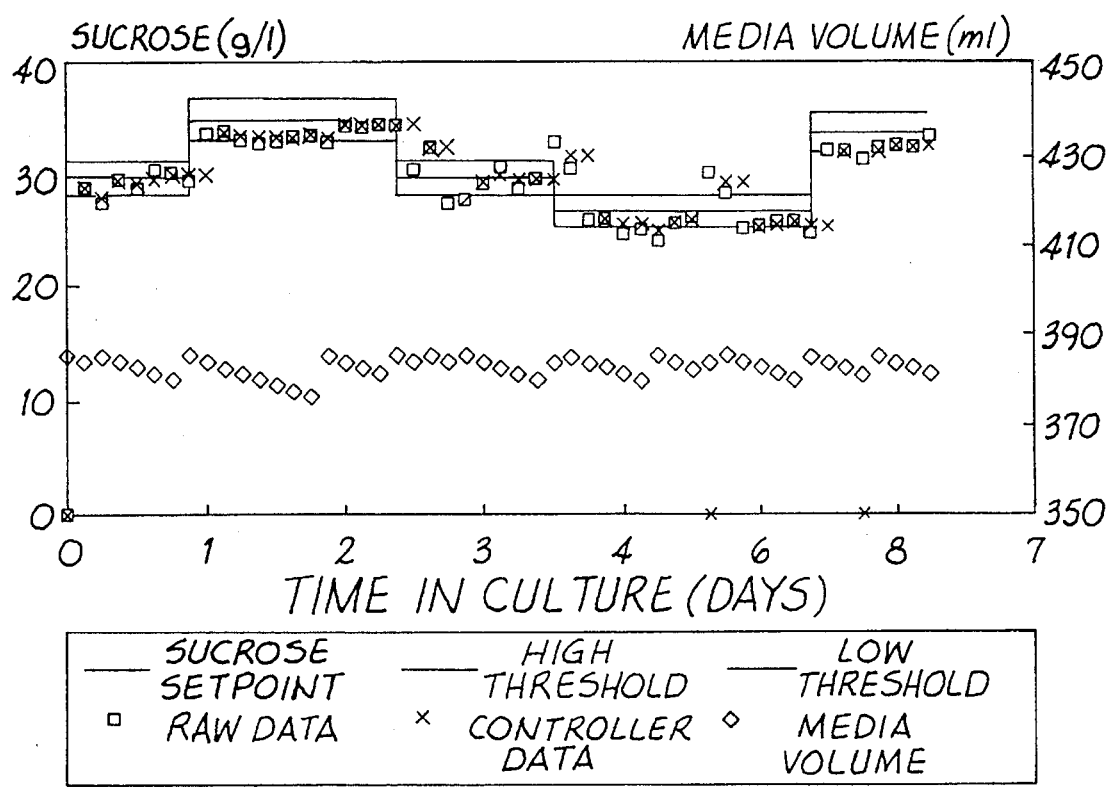
FIG. 6 is a graphical representation of the results in Example 1 using the system and process of the present invention.

Sucrose concentration and media volume control data obtained during testing of the micropropagation system's response to setpoint changes and plant disturbances are shown graphically in FIG. 6. In general, the system was able to follow sucrose setpoint changes and correct system disturbances without difficulty. Sampled media aliquots were replaced when the calculated bioreactor media volume passed below the 2.5 percent operational threshold as described above. Differences observed immediately after each step change disturbance between unfiltered, "raw" sucrose data and filtered controller sucrose data demonstrate the function of the filtering algorithm. Individual step changes and disturbances in the sucrose concentration setpoint caused the system to detect an error when bioreactor media was next sampled. However, the filtering algorithm smoothed the effects of this error, causing the perturbations observed. The effects of errant data points on system performance were also minimized by the filter, enhancing system response and stability.

EXAMPLE 2

This experiment compared the growth of Stage 1, tobacco tissue cultured in the micropropagation system of the present invention with the growth of explants cultured in a system which automatically monitored growth media sucrose levels but could only maintain constant volume levels in the bioreactor and could not change or maintain sucrose concentration. In this second system complete replenishment occurred at periodic intervals. These two systems were also compared to explants cultured in a liquid/membrane bioreactor only with nutrient replenishment at 7-day intervals. A single bioreactor containing 10 membrane rafts was used in each of the three systems. Bioreactor media were automatically sampled for sucrose analysis at 3-hour intervals in the micropropagation system of the present invention and in the above described second system with all control actions being taken at this same time.

Tobacco explants were transferred into each bioreactor from agar-based cultures initiated 6–7 days earlier on Petri plates. Four leaf disks were inoculated into each membrane raft. The base medium formulation consisted of 30 g/l sucrose, 4.4 g/l Murashige and Skoog salts, 0.1 g/l myo-inositol, 0.0004 g/l thiamine HCl and 0.0022 g/l benzyladenine (BA) at a pH of 5.7. While in the second and third systems above, media were manually mixed prior to system setup, the micropropagation system of the present invention media was blended under computer control from stock reservoir solutions consisting of:

(1) 200 g/l sucrose, pH 5.7, (2) 13.2 g/l Murashige and Skoog salts, 0.30 g/l myo-inositol, 0.0012 g/l thiamine HCl, 0.0066 g/l BA, pH 5.7, (3) distilled, deionized water A bioreactor medium volume setpoint of 385 ml was used in the micropropagation system and the second system. A sucrose setpoint of 30 g/l was used in the micropropagation system. The liquid/membrane bioreactor treatment, the third system, had a chamber media volume of 350 ml.

All components of the bioreactor systems, except the media sterilization and sampling filters, were assembled prior to autoclave sterilization. The filters were subsequently connected to the system under laminar flow conditions. Media sterilization was accomplished through filtration with a manufacturer-presterilized filter. Following culture setup, plant material in the third system was incubated at 25±2 degrees C., with an intensity of 22 to 26 umol m$^{-2}$sec$^{-1}$ and a 16-hour photoperiod under cool white fluorescent lights. The micropropagation and second system treatments were incubated at 25±2 degrees C. and 45 to 50 umol m$^{-2}$sec$^{-1}$ light intensity with an identical photoperiod. The initial weight of explant tissue subcultured into all system treatments was measured along with the tissue fresh weight following completion of a 28-day culture cycle.

Data collected throughout the 28-day tobacco initiation experiment showed the micropropagation system of the present invention to operate without difficulty. However, contaminated tissue was observed in two of the membrane rafts on day-11 and promptly removed from the chamber without compromising overall system asepsis. Media sucrose concentration was accurately controlled to within plus or minus 5 percent while replacing sampled media aliquots. However, visual observations of the media volume contained within the bioreactor chamber, showed a decrease with time. An additional 30 ml of fresh media were pumped into the bioreactor chamber on day-19 to prevent the volume from becoming critically low, biasing explant growth response. This media volume decrease was thought to have been due to rapid uptake by explants.

The growth response of tissues cultured in the micropropagation system of the present invention was superior to all other culture treatments. Explants showed both large fresh weight increases as well as the development of large numbers of shoots. The results are as follows:

| Treatment | Final Fresh Weight (g) | Total Fresh Weight Gain (g) |
| --- | --- | --- |
| Liquid/Membrane Bioreactor | 12.48 ± 1.96 | 12.16 ± 1.98 |
| Constant Volume Micropropagation System | 2.48 ± 0.26 | 2.34 ± 0.26 |
| Micropropagation System of the present invention | 18.72 ± 2.25 | 18.32 ± 2.24 |

An analysis of variance found final fresh weights and total fresh weight gains were significantly different among all treatments. Average fresh weight gain for explant tissues cultured in the micropropagation system of the present invention were 1.5 times greater than the liquid/membrane bioreactor grown tissue and 7.8 times greater than explants from the constant volume system. However, a portion of the large differences in growth between the micropropagation system of the present invention and the constant volume system may be attributed to the condition of the parent plants from which the tissues were taken.

These and other modifications and variations to the present invention may be practiced by those of ordinary skill in the art without departing from the spirit and scope of the present invention which is more particularly set forth in the appended claims. In addition, it should be understood that aspects of the various embodiments may be interchanged both in whole or in part. It will also be understood that although the forms of the invention shown and described herein constitute a preferred embodiment of the invention, it is not intended to illustrate all possible forms of the invention. The words used are words of description rather than of limitation. Various changes and variations may be made to the present invention without departing from the spirit and scope of the following claims.

What is claimed is:

1. A plant micropropagation system for automated growth of plant tissue, said system comprising:

a plurality of reservoirs for containing various preselected growth media subcomponents;

an enclosed bioreactor impermeable to microorganisms in communication with said reservoirs for receiving growth media subcomponents therefrom, said bioreactor adapted to completely enclose plant tissue therein and to supply growth media to said tissue for promoting the growth thereof, said bioreactor further including gas exchange means for allowing gases to enter and exit said bioreactor;

flow control means for regulating the flow of said subcomponents into said bioreactor;

a chemical analyzer for sampling said plant growth media from said bioreactor at periodic intervals and for analyzing said media; and a controller in operative association with said flow control means, said controller electronically receiving data from said analyzer based on analysis of said media and, based on said data, controlling said flow control means for selectively feeding certain of said subcomponents to said bioreactor.

2. A plant micropropagation system as defined in claim 1, wherein said flow control means includes valve means in operative association with each of said plurality of reservoirs for controlling the flow of said subcomponents from said reservoirs; and a pump means cooperative with said valve means for pumping said subcomponents from said reservoirs to said bioreactor.

3. A plant micropropagation system as defined in claim 1, wherein said growth media contains organic carbon for promoting the heterotrophic growth of plant tissue and wherein said chemical analyzer is a sugar analyzer for analyzing the sugar concentration contained within said growth media.

4. A plant micropropagation system as defined in claim 1, wherein said system is completely enclosed for preventing contaminants from contaminating said growth media or any plant tissue contained with said bioreactor, said system including conduit means for interconnecting said reservoirs, said bioreactor, and said chemical analyzer.

5. A plant micropropagation system as defined in claim 1, wherein said gas exchange means of said bioreactor comprises gas exchange filters, said filters being permeable to gases but impermeable to contaminants.

6. A plant micropropagation system as defined in claim 1, further including at least one membrane received within said bioreactor for supporting tissue thereon and for contact with said growth media.

7. A plant micropropagation system as defined in claim 1, further comprising fluid circulation means in operative association with said bioreactor, said circulation means for circulating and mixing said plant growth media.

8. A plant micropropagation system as defined in claim 1, further including means associated with said bioreactor for removing excess growth media contained within said bioreactor.

9. A plant micropropagation system as defined in claim 8, further comprising control means associated with said media removal means for maintaining a predetermined volume of said growth media within said bioreactor.

10. A plant micropropagation system for promoting the heterotrophic growth of plant tissue, said system comprising:

at least one bioreactor for containing growing plant tissue, said bioreactor adapted to circulate a plant growth media for absorption by said plant tissue;

a plurality of reservoirs for containing various preselected chemical subcomponents for controlled blending into said plant growth media, said reservoirs being connected to said bioreactor for supplying said subcomponents thereto, wherein said reservoirs contain at a least a sugar solution and a liquid nutrient solution;

valve means and a supply pump for pumping predetermined amounts of said subcomponents into said bioreactor, said subcomponents being fed to said bioreactor one at a time;

a fluid outlet and a waste pump for pumping spent growth media out of said bioreactor;

mixing means for mixing said plant growth media;

a sugar analyzer for periodically receiving a small aliquot of said plant growth media from said system for analysis, wherein said sugar analyzer analyzes said aliquot for sugar concentration; and a controller for receiving said sugar analysis from said analyzer and, based on said analysis, for selectively controlling said valve means, said supply pump and said waste pump for supplying certain of said subcomponents to said bioreactor in selected amounts and for removing spent growth media from said bioreactor, wherein said controller automatically maintains the sugar concentration of said growth media within a preset range and maintains a preset volume of said growth media within said bioreactor.

11. A plant micropropagation system as defined in claims 10, further comprising at least one membrane support received within said bioreactor for supporting plant tissue thereon, said support including a plant support membrane, wherein tissue received thereon can absorb said growth media through said membrane.

12. A plant micropropagation system as defined in claim 10, wherein said bioreactor comprises a container impermeable to microorganisms and includes gas exchange filters, said filters being permeable to gases while remaining impermeable to microorganisms.

13. A plant micropropagation system as defined in claim 10, further comprising a carbon dioxide source in communication with said bioreactor for supplying carbon dioxide thereto.

14. A plant micropropagation system as defined in claim 10, further comprising additional chemical analyzers for receiving aliquots of said plant growth media from said bioreactor and for analyzing said aliquots for the concentration of other chemical components contained within said growth media, wherein said analysis is transmitted to said controller for also maintaining the concentration of said chemical components within a preset range.

15. A plant micropropagation system as defined in claim 10, wherein said mixing means includes a circulation pump and a corresponding conduit loop having a bioreactor inlet and a bioreactor outlet for circulating and mixing said plant growth media into and out of said bioreactor.

16. A plant micropropagation system as defined in claim 10, wherein said controller includes a processing means for receiving input from said sugar analyzer, said processing means being operative to enter said input into a processing sequence, said processing sequence comprising the steps of:

a) determining whether said input is within a preset range; and b) if said input is outside said preset range, entering said input into an algorithm for determining how to control said valve means, said supply pump, and said waste pump for adjusting a value represented by said input to within said preset range.

17. A process for heterotrophically growing plant tissue, said process comprising the steps of:

placing plant tissue in a bioreactor that is impermeable to microorganisms;

supplying a preset number of subcomponent solutions in predetermined concentrations to said bioreactor;

blending predetermined amounts of certain of said subcomponent solutions to form a plant growth media for circulation within said bioreactor and for absorption by said plant tissue, said plant growth media containing organic carbon for promoting the heterotrophic growth of said plant tissue;

analyzing said plant growth media at periodic intervals for determining the concentration of a particular component within said growth media; and sending the analysis from said analyzing step to a controller for processing said analysis and for automatically feeding said subcomponent solutions to said bioreactor for maintaining the concentration of said particular component in said growth media within a preset range while maintaining a preset volume of growth media within said bioreactor.

18. A process as defined in claim 17, wherein said concentration of said particular component is the concentration of sugar within said growth media.

19. A process as defined in claim 17, further comprising the step of completely draining and replenishing said plant growth media within said bioreactor at predetermined periodic intervals, said draining and replenishing step being automatically controlled by said controller.

20. A process as defined in claim 17, further comprising the step of placing said plant tissue onto a membrane within said bioreactor, said plant tissue absorbing said plant growth media through said membrane.

21. A process as defined in claim 17, wherein, when said plant tissue is initially enclosed within said bioreactor, said plant tissue is incapable of photosynthesizing at a rate that will sustain life.

* * * * *